United States Patent [19]

Higuchi et al.

[11] Patent Number: 4,794,201

[45] Date of Patent: Dec. 27, 1988

[54] PROCESS FOR PREPARATION OF P-HALOGENO-MONOALKYLBENZENES

[75] Inventors: Yasushi Higuchi; Suzuki, both of Shizuoka, Japan

[73] Assignee: Ihara Chemical Industriy Co., Ltd., Tokyo, Japan

[21] Appl. No.: 11,246

[22] Filed: Feb. 5, 1987

Related U.S. Application Data

[63] Continuation of Ser. No. 758,250, Jan. 24, 1985, abandoned, which is a continuation-in-part of Ser. No. 715,777, Mar. 26, 1985, abandoned, which is a continuation of Ser. No. 564,527, Dec. 22, 1983, abandoned.

[51] Int. Cl.$^4$ .............................................. C07C 17/12
[52] U.S. Cl. ..................................... 570/208; 570/206
[58] Field of Search ................................ 570/206, 208

[56] References Cited

U.S. PATENT DOCUMENTS

| | | | |
|---|---|---|---|
| 2,998,459 | 8/1961 | Baker et al. | 570/207 |
| 3,216,789 | 11/1965 | Breck et al. | 23/113 |
| 3,706,694 | 12/1972 | Young | 502/74 |
| 3,752,856 | 8/1973 | Nacy et al. | 570/206 |
| 3,945,943 | 3/1976 | Ward | 502/64 |

FOREIGN PATENT DOCUMENTS

| | | | |
|---|---|---|---|
| 112722 | 7/1984 | European Pat. Off. | 570/306 |
| 2721640 | 11/1978 | Fed. Rep. of Germany | 570/208 |
| 31627 | 2/1982 | Japan | 570/206 |
| 77631 | 5/1982 | Japan | 570/206 |
| 47903 | 3/1979 | U.S.S.R. | 570/208 |

OTHER PUBLICATIONS

Translator's Declaration and Translation of Japanese patent No. 77631.
D. W. Breck, *Zeolite Molecular Sieve*, Wiley, N.Y., 1974, Chapters 2 and 4 (exerpted).
M. Che and A. J. Tench, *Adv. in Catalysis 32* 1 (1983), p. 60.
N. Hara and H. Takahashi, *Zeolite—Basis and Application* Kodansha, partial Translation.
*Chem. and Engineering News*, American Chemical Society, Feb. 17, 1986, p. 50.
J. M. Newsam, *Science*, 231, 1093 (1986).
J. D. Roberts and M. C. Caserio, *Basis Principles of Organic Chemistry*, W. A. Benjamin, N.Y., 1765 pp. 800–801.
Weast, *Handbook of Chemistry and Physics*, 54th ed., CRC Publishing, Cleveland (1973), pp. C–145, C–146, C–159, C–161, C–164, C–512.
P. B. Weisz and V. J. Frilette, *J. Phys. Chem.*, 64, 382 (1960).

Primary Examiner—Werren B. Lone
Attorney, Agent, or Firm—Oblon, Fisher, Spivak, McClelland & Maier

[57] ABSTRACT

A p-halogeno-monoalkylbenzene is prepared at an enhanced selectivity by halogenating a monoalkylbenzene in the liquid phase in the presence of an L-type zeolite catalyst.

21 Claims, No Drawings

PROCESS FOR PREPARATION OF P-HALOGENO-MONOALKYLBENZENES

CROSS-REFERENCE TO RELATED APPLICATION

This application is a continuation of application Ser. No. 758,250, filed on July 24, 1985, now abandoned, which is a continuation-in-part application of application Ser. No. 715,777, filed on Mar. 26, 1985, now abandoned, which is a continuation application of application Ser. No. 564,527 filed on Dec. 22, 1983, now abandoned.

BACKGROUND OF THE INVENTION (1) Field of the Invention

This invention relates to a process for the preparation of a p-halogeno-monoalkylbenzene. More particularly, the present invention relates to a process for preparing a p-halogeno-monoalkylbenzene at a high selectivity by nuclear halogenation of a monoalkylbenzene in a liquid phase in the presence of a specific zeolite catalyst.

(2) Description of the Prior Art

Nuclear halides of monoalkylbenzenes are valuable as starting materials for the synthesis of medicines, agricultural chemicals, and other various organic compounds. Among nuclear halides of monoalkylbenzenes, p-chloro-monoalkylbenzenes, for example, p-chlorotoluene, are in especially great demand.

As a conventional process for the preparation of p-halogeno-monoalkylbenzenes, there is known a process in which a monoalkylbenzene is subjected to nuclear halogenation by using a Lewis acid such as antimony chloride, ferric chloride or aluminum chloride as a catalyst and a chlorine gas as a chlorinating agent. In this process, an o-chloro-monoalkylbenzene and a p-chloro-monoalkylbenzene are formed as the predominant product and an m-chloro-monoalkylbenzene and polychlorinated substitution products are formed as by-products. It is impossible, however, to prepare the p-chloro-monoalkylbenzene in a yield higher than 40%.

Various catalysts have therefore been developed so as to produce p-chloro-monoalkylbenzenes in high yields. For example, in a process using a Lewis acid and sulfur or selenium as the catalyst, a p-chloromonoalkylbenzene is obtained in a yield of 45% to 52%. In a process using a Lewis acid and thianthrene as the catalyst, a p-chloro-monoalkylbenzene is obtained in a yield of 55% to 60% (see U.S. Pat. No. 4,031,147 and British Patent No. 7,605,039). Furthermore, in a process using a Lewis acid and phenoxathiin as the catalyst, a p-chloro-monoalkylbenzene is obtained in a yield of 52% to 60% (see European Patent No. 63384).

As another process for preparing a p-halogenomonoalkylbenzene, ther is known a process in which silica gel is used as the catalyst and sulfuryl chloride is used as the halogenating agent. In this process, a p-chloro-monoalkylbenzene is obtained in a yield of 50% [see Journal of Synthetic Organic Chemistry, 37, page 690 (1979) (Japan)].

However, all of these known processes are still insufficient in the selectivity to p-chloromonoalkylbenzenes.

SUMMARY OF THE INVENTION

It is a primary object of the present invention to provide a process by which a p-halogeno-monoalkylbenzene can be prepared at a higher selectivity than in the conventional processes.

In accordance with the present invention, there is provided a process for preparing a p-halogeno-monoalkylbenzene by halogenating a monoalkylbenzene, the alkyl group of which has 1 to 4 carbon atoms, in a liquid phase in the presence of a zeolite catalyst. This process is characterized in that the catalyst used is an L-type zeolite represented by the following formula:

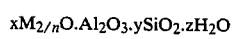

wherein M represents at least one exchangeable metal cation, n represents the valence of M, x is a number of 0.9 to 1.3, y is a number of 4.0 to 8.0 and z is a number of from 0 to about 9.

DESCRIPTION OF THE PREFERRED EMBODIMENTS

The L-type zeolite used in the process of the present invention is a synthetic zeolite such as chabazite, which has hexagonal crystalline system and which belongs to a chabazite group. The fundamental unit structure of the L-type zeolite is cancrinite which is an undecahedron consisting of six four-membered rings and five six-membered rings, each composed of aluminum, silicon and oxygen atoms. The L-type zeolite has a crosslinked structure composed of six cancrinite units which are crosslinked with oxygen and which have in the central portion thereof a pore defined by a twelve-membered ring. The pore is characterized as extending unidimensionally and having a diameter of 7 to 8 angstroms.

The composition of the L-type zeolite is represented by the general formula:

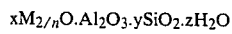

wherein M represents at least one exchangeable metal cation, n represents the valence of M, x is a number of 0.9 to 1.3, y is a number of 4.0 to 8.0 and z is a number of from 0 to about 9.

Minor variations in the molar ratios of the oxides within the ranges indicated by the above formula may be made without significant change of the crystal structure of the zeolite. For example, the molar ratio of silica ($SiO_2$) to alumina ($Al_2O_3$) may vary from 4.0 to 8.0, preferably from 5.0 to 7.0.

The L-type zeolite is more completely described in U.S. Pat. No. 3,216,789 wherein a conventional description of the L-type zeolite is given with respect to the X-ray diffraction spectrum.

An L-type zeolite is conventionally synthesized in the potassium form. Namely, most of the M cations in the general formula given previously are potassium. The M cations are exchangeable so that a given L-type zeolite, e.g., an L-type zeolite in the potassium form, can be used to obtain an L-type zeolite containing other cations, by subjecting the L-type zeolite to ion exchange treatment in an aqueous solution of appropriate salts. However, it is difficult to exchange more than about 80% of the original cation, e.g., potassium since some exchangeable cations in the zeolite are in sites which are difficult for the reagents to reach.

The exchangeable metal cation M in the L-type zeolite used in the present invention is preferably an exchangeable cation selected from th ions of potassium, sodium and metals of IA, IIA, IIIA, IVA and VA groups in the periodic table. Potassium and sodium are more preferable. The catalyst may be used either in the uncalcined state or in the calcined state.

Various linear and branched monoalkylbenzenes having 1 to 4 carbon atoms in the alkyl group can be halogenated according to the process of the present invention.

For preparing a p-halogeno-monoalkylbenzene according to the process of the present invention, an L-type zeolite is added to a monoalkylbenzene in an amount of at least 0.01 g, preferably 0.1 to 50 g, and more preferably 1 to 30 g, per mole of the monoalkylbenzene so that the mixture can be stirred. A halogenating agent is introduced in the mixture at a temperature lower than the boiling point to effect reaction between the monoalkylbenzene and the halogenating agent. A reaction solvent may be used if desired. The reaction temperature is not particularly critical, but it is preferred that the reaction be carried out at a temperature higher than 0° C. but lower than the boiling point, and more preferably from 50° C. to 90° C.

Halogenating agents customarily used in this field may be used in the present invention. For example, a halogen such as chlorine gas or bromine and sulfuryl halides such as sulfuryl chloride may be used. Among these, sulfuryl chloride is most preferably used.

An inert gas such as nitrogen may be used for the reaction. The reaction may be carried out under an elevated or reduced pressure, but ordinarily, the reaction is carried out under atmospheric pressure.

According to the process of the present invention, the p-position of a monoalkylbenzene can be effectively halogenated at a high selectivity while controlling halogenation at the o-position of a monoalkylbenzene. Moreover, the process of the present invention is advantageous in that formation of side chain halides of monoalkylbenzenes such as benzyl halides and polynuclear halides can be greatly controlled. Furthermore, the reaction add post treatment operations are very simple and the catalyst can be used repeatedly. Theefore, the process of the present invention is very suitable for the production of p-halogeno-monoalkylbenzenes.

The process of the present invention will now be described in detail with reference to the following examples.

EXAMPLE 1

(Chlorination of toluene using nn L-type zeolite "TSZ-502" catalyst)

A 200-ml reaction flask equipped with a cooling tube, a thermometer, a stirrer and a blow tube was charged with 2.5 g of an L-type zeolite "TSZ-502" (trademark supplied by TOYO SODA MANUFACTURING CO., LTD., Japan) and 46.1 g (0.5 mole) of toluene. The mixture was stirred at 70° C. for 30 minutes in a current of $N_2$. Then, chlorine wss blown into the flask at a rate of 0.125 mol/hr. The reaction was conducted for 4 hours. The amount of chlorine blown corresponded to the theoretical amount. After completion of the reaction, the obtained liquid mixture was analyzed by gas chromatography. The results are shown in Table I.

The L-type zeolite TSZ-502 had the following composition and an average micropore diameter of 8 angstroms.

| | |
|---|---|
| $SiO_2$ | 64.6% by weight |
| $Al_2O_3$ | 17.8% by weight |
| $Na_2O$ | 0.15% by weight |
| $SiO_2/Al_2O_3$ (molar ratio) | 6.2 |
| $K_2O$ | 15.9% by weight |

EXAMPLE 2

(Chlorination of toluene using an L-type zeolite "TSZ-504" catalyst)

Following the same procedure as described in Example 1, toluene was chlorinated wherein an L-type zeolite "TSZ-504" (trademark; supplied by TOYO SODA MANUFACTURING CO., LTD., Japan) was used instead of TSZ-502 with all other conditions remaining the same. The results are shown in Table I.

The L-type zeolite TSZ-504 had the following composition and an average micropore diameter of 8 angstroms.

| | | |
|---|---|---|
| $SiO_2$ | 62.6% | by weight (on dry base) |
| $Al_2O_3$ | 18.0 | by weight (on dry base) |
| $Na_2O$ | 0.097 | by weight (on dry base) |
| $SiO_2/Al_2O_3$ (molar ratio) | 5.9 | |
| $K_2O$ | 18.6% | by weight (on dry base) |

EXAMPLE 3

(Chlorination of toluene using an L-type zeolite "TSZ-505" catalyst)

Following the same procedure as described in Example 1, toluene was chlorinated wherein an L-type zeolite "TSZ-505" (trademark; supplied by TOYO SODA MANUFACTURING CO., LTD. Japan) was used instead of TSZ-502 with all other conditions remaining the same. The results are shown in Table I.

The L-type zeolite TSZ-505 had the following composition and an average micropore diameter of 8 angstroms.

| | | |
|---|---|---|
| $SiO_2$ | 63.2% | by weight (on dry base) |
| $Al_2O_3$ | 17.6 | by weight (on dry base) |
| $Na_2O$ | 0.1 | by weight (on dry base) |
| $SiO_2/Al_2O_3$ (molar ratio) | 6.1 | |
| $K_2O$ | 17.6% | by weight (on dry base) |

EXAMPLE 4

(Chlorination of toluene using an L-type zeolite "TSZ-506" catalyst)

Following the same procedure as described in Example 1, toluene was chlorinated wherein an L-type zeolite "TSZ-506" (trademark; supplied by TOYO SODA MANUFACTURING CO., LTD., Japan) was used instead of TSZ-502 with all other conditions remaining the same. The results are shown in Table I.

The L-type zeolite TSZ-506 had the following composition and an average micropore diameter of 8 angstroms.

| | | |
|---|---|---|
| $SiO_2$ | 64.1% | by weight (on dry base) |
| $Al_2O_3$ | 18.4 | by weight (on dry base) |
| $Na_2O$ | 0.202 | by weight (on dry base) |
| $SiO_2/Al_2O_3$ (molar ratio) | 5.9 | |
| $K_2O$ | 17.6% | by weight (on dry base) |

COMPARATIVE EXAMPLE 1

(Chlorination of toluene using a K-Offretite zeolite "TSZ-451" catalyst)

Following the same procedure as described in Example 1, toluene was chlorinated wherein a K-Offretite zeolite "TSZ-451" (trademark; supplied by TOYO SODA MANUFACTURING CO., LTD., Japan) was used instead of TSZ-502 with all other conditions remaining the same. The results are shown in Table I.

The K-Offretite zeolite TSZ-451 had a $SiO_2/Al_2O_3$ molar ratio of 7.4 and an average micropore size of 6 angstroms.

COMPARATIVE EXAMPLE 2

(Chlorination of toluene using a Na-TMA-Ω zeolite catalyst)

Following the same procedure as mentioned in Example 1, toluene was chlorinated wherein a Na-TMA-Ω zeolite "ELZ-Ω-5" (trademark; supplied by Union Carbide Corp.) was used instead of TSZ-502 with all other conditions remaining the same. The results are shown in Table I.

The Na-TMA-Ω zeolite had an average micropore size of 8 angstroms.

COMPARATIVE EXAMPLE 3

(Chlorination of toluene using an X-type zeolite catalyst)

Following the same procedure as described in Example 1, toluene was chlorinated wherein an X-type zeolite "LINDE 13X" (trademark supplied by Union Carbide Corp.) was used instead of TSZ-502 with all other conditions remaining the same. The results are shown in Table I.

The LINDE 13X zeolite had a $SiO_3/Al_2O_3$ molar ratio of 2.5 and an average micropore size of 10 angstroms.

COMPARATIVE EXAMPLE 4

(Chlorination of toluene using a Y-type zeolite catalyst)

Following the same procedure as described n Example 1, toluene was chlorinated wherein a Y-type zeolite "LZ-Y52" (trademark supplied by Union Carbide Corp.) was used instead of TSZ-502 with all other conditions remaining the same. The results are shown in Table 1.

The Y-type zeolite LZ-Y52 had an average micropore diameter of 8 angstroms and the following composition.

| | | |
|---|---|---|
| $SiO_2$ | 63.8% | by weight (on dry base) |
| $Al_2O_3$ | 22.9 | by weight (on dry base) |
| $Na_2O$ | 13.0 | by weight (on dry base) |
| $SiO_2/Al_2O_3$ (molar ratio) | 4.74 | |

COMPARATIVE EXAMPLE 5

(Chlorination of toluene using an amorphous alumina-silicate catalyst)

Following the same procedure as described in Example 1, toluene was chlorinated wherein an amorphous alumino-silicate having a $SiO_2$ content of 65–70% (supplied by Nikki Chemica Co., Ltd., Japan) was used instead of TSZ-502 with all other conditions remaining the same. The results are shown in Table I.

COMPARATIVE EXAMPLE 6

(Chlorination of toluene using an X-type zeolite "TSZ-201" catalyst)

Following the same procedure as described in Example 1, toluene was chlorinated wherein an X-type zeolite "TSZ-201" (trademark; supplied by TOYO SODA MANUFACTURING CO., LTD., Japan) was used instead of TSZ-502 with all other conditions remaining the same. The results are shown in Table I.

The X-type zeolite used for the reaction had the following chemical composition (as determined by atomic absorption spectroscopy):

$SiO_2$: 47.2% by weight (dry base)
$Al_2O_3$: 31.7% by weight (dry base)
$Na_2O_3$: 18.5% by weight (dry base)
$SiO_2/Al_2O_3$ molar ratio: 2.5

TABLE I

| Example No. | Catalyst | Conversion of toluene (%) | O/P ratio | Selectivity to p-chlorotoluene (%) |
|---|---|---|---|---|
| Example 1 | L-type, TSZ-502 | 97.90 | 0.501 | 63.92 |
| Example 2 | L-type, TSZ-504 | 97.08 | 0.504 | 64.00 |
| Example 3 | L-type, TSZ-505 | 97.75 | 0.507 | 65.25 |
| Example 4 | L-type, TSZ-506 | 98.00 | 0.493 | 64.50 |
| Comparative Example 1 | K-Offretite, TSZ-451 | 88.27 | 1.137 | 44.01 |
| Comparative Example 2 | Na, TMA-Ω, ELZ-Ω-5 | 91.97 | 1.711 | 35.71 |
| Comparative Example 3 | X-type, LINDE 13X | 82.3 | 1.774 | 27.6 |
| Comparative Example 4 | Y-type, LZ-Y52 | 91.0 | 1.293 | 41.5 |
| Comparative Example 5 | Amorphous aluminosilicate | 94.0 | 1.662 | 36.1 |
| Comparative Example 6 | X-type, TSZ-201 | 85.0 | 1.74 | 33.1 |

As in seen from the comparison of Examples 1 through 4 with Comparative Examples 1 thgough 6, when the chlorination of toluene is carried out in a liquid phase by using an L-type zeolite, p-chlorotoluene is obtained in a much higher selectivity than those which are attained when the chlorination of toluene is carried out by using other catalysts such as an X-type zeolite (Comparative Example 3 and 6), a Y-type zeolite (Comparative Example 4), a K-Offretite zeolite (Comparative Example 1), Na-TMA-Ω zeolite (Comparative Example 2) and amorphous aluminosilicate (Comparative Example 5).

It was common knowledge to a person skilled in the art that nuclear halogenation of an alkylbenzene using a zeolite catalyst cannot advantageously be carried out in a liquid phase because hydrogen halide generated is adsorbed by the zeolite catalyst with the result of deterioration of the zeolite catalyst, and thus, nuclear halogenation of an alkylbenzene using a zeolite catalyst should be carried out not in a liquid phase but in a vapor phase. This is substantiated by Comparative Examples 1 through 6. It is surprising and contrary to the common knowledge that nuclear halogenation of an alkylbenzene using an L-type zeolite catalyst can be advantageously carried out in a liquid phase.

EXAMPLES 5 through 9

(Chlorination of toluene using an L-type zeolite "TSZ-502" catalyst)

A 200-ml reaction flask equipped with a cooling tube, a thermometer, a stirrer and a blow tube was charged with an L-type zeolite "TSZ-502" (trademark supplied by TOYO SODA MANUFACTURING CO., LTD., Japan) and 92.1 g (1 mole) of toluene. The mixture was stirred for 30 minutes in a current of $N_2$. Then, chlorine was blown into the flask at a rate of 0.29 mole per hour. The reaction was conducted for 4 hours. After completion of the reaction, the obtained liquid mixture was analyzed by gas chromatography. The results are shown in Table II. The reaction temperature and the amount of the L-type zeolite used are also shown in Table II.

TABLE II

| Example No. | Amount (g) of L-type zeolite | Reaction temperature (°C.) | Conversion (%) | O/P Ratio |
| --- | --- | --- | --- | --- |
| 5 | 5 | 50 | 90.7 | 0.51 |
| 6 | 5 | 70 | 97.9 | 0.50 |
| 7 | 1 | 70 | 84.5 | 0.49 |
| 8 | 5 | 90 | 98 | 0.48 |
| 9 | 5 | 110–120 | 95 | 0.56 |

The L-type zeolite used for the reaction had the following chemical composition (as determined by atomic absorption spectroscopy):
$SiO_2$: 64.6% by weight (dry base)
$Al_2O_3$: 17.8% by weight (dry base)
$Na_2O$: 0.15% by weight (dry base)
$SiO_2/Al_2O_3$ molar ratio: 6.2
$K_2O$: 15.9% by weight (dry base)

EXAMPLE 10

(Chlorination of toluene using an L-type zeolite "TSZ-502" catalyst)

The reaction was carried out in the same manner as described in Example 5, and then the catalyst was used again for the reaction could be advanced normally, and the O/P ratio was 0.52. The catalyst could be used further.

EXAMPLES 11 through 14

(Chlorination of various monoalkylbenzenes using an L-type zeolite "TSZ-502" catalyst)

The reactions were carried out in the same manner as described in Example 5, except that the alkylbenzenes shown in Table III were used instead of toluene used in Example 5, whereby p-halogeno-monoalkylbenzenes, shown in Table III, were obtained. The obtained results are shown in Table III. Incidentally, the O/P ratio in Table III indicates the o-chloro-monoalkylbenzene/p-chloro-monoalkylbenzene molar ratio in the formed nuclear chloride of monoalkylbenzene.

TABLE III

| Example No. | Monoalkylbenzene to be halogenated | Conversion (%) of alkylbenzene | P-halogeno-monoalkylbenzene | O/P ratio | Selectivity to p-chloro-monoalkylbenzene |
| --- | --- | --- | --- | --- | --- |
| 11 | Ethylbenzene | 94.9 | Chloroethylbenzene | 0.33 | 71.97 |
| 12 | Isopropylbenzene | 90.7 | Chloroisopropyl benzene | 0.26 | 72.28 |
| 13 | Sec-Butylbenzene | 77.4 | Chloro-sec-butyl benzene | 0.17 | 75.17 |
| 14 | tert-Butylbenzene | 70.5 | Chloro-tert-butyl benzene | 0.06 | 82.80 |

EXAMPLE 15

(Chlorination of toluene using an L-type zeolite "TSZ-502" catalyst and a sulfuryl chloride halogenating agent)

The reaction was carried out in the same manner as described in Example 5, except that sulfuryl chloride was used as the halogenating agent instead of the chlorine gas used in Example 5 and 35.2 g (1.002 moles) of sulfuryl chloride was dropped over a period of 3.5 hours.

It was found that the conversion of toluene was 99.6%, the O/P ratio was 0.32, the selectivity to p-chlorotoluene was 73.10%, and benzyl chloride was formed as a by-product in a yield of 0.8%.

We claim:

1. A process for preparing a p-monohalogenomonoalkylbenzene, the alkyl group of which has 1 to 4 carbon atoms, comprising:
   (i) combining a mono-($C_{1-4}$)-alkylbenzene with a halogenating agent which is one member selected from the group consisting of chlorine, bromine and sulfuryl halides, in the liquid phase in the presence of a catalyst, said catalyst being a L-type zeolite represented by the following formula:

$xM_{2/n}O.Al_2O_3.ySiO_2.zH_2O$ wherein M represents at least one exchangeable metal cation selected from the group consisting of the ions of potassium, sodium and metals of IA, IIA, IIIA, IVA and VA groups in the Periodic Table of the Elements, n represents the valence of M, x is a number between 0.9 and 1.3, y is a number between 4.0 and 8.0, and z is a number of from 0 to about 9; and
   (ii) obtaining said p-halogenomonoalkylbenzene.

2. A process according to claim 1 wherein the L-type zeolite has pores having a diameter of 7 to 8 angstroms, said pores being defined by a twelve membered ring.

3. A process according to claim 1 wherein y in the formula is a number of 5.0 to 7.0.

4. A process according to claim 1 wherein the exchangeable metal cation M is an alkali metal ion.

5. A process according to claim 1 wherein the exchangeable cation M is selected from the group consisting of potassium ion and sodium ion.

6. A process according to claim 1 wherein the exchangeable metal cation M is potassium ion.

7. A process according to claim 1, wherein the amount of the L-type zeolite used is at least 0.01 g per mole of the monoalkylbenzene.

8. A process according to claim 1, wherein the amount of the L-type zeolite used is in the range of from 0.1 to 50 g per mole of the monoalkylbenzene.

9. A process according to claim 1, wherein the amount of the L-type zeolite used is in the range of from 1 to 30 g per mole of the monoalkylbenzene.

10. A process according to claim 1, wherein chlorine gas or bromine is used as a halogenating agent.

11. A process according to claim 1, wherein a sulfuryl halide is used as a halogenating agent.

12. A process according to claim 5, wherein the sulfuryl halide is sulfuryl choloride.

13. A process according to claim 1, wherein the monoalkylbenzene is halogenated at a temperature higher than 0° C. but lower than its boiling point.

14. A process according to claim 1, wherein the monoalkylbenzene is halogenated at a temperature of from 50° to 90° C.

15. A process for obtaining with high selectivity a para-monohalogeno-mono($C_{1-4}$)alkylbenzene from a mono($C_{1-4}$)alkylbenzene, said process comprising:
   (a) combining an L-type zeolite and a mono($C_{1-4}$)-alkylbenzene in a ratio of from 0.01 gram to 50 grams of zeolite per mole of the mono($C_{1-4}$)alkylbenzene to obtain a reaction mixture;
   (b) adjusting the temperature of the said reaction mixture to a temperature of from 0° C. to a temperature below the boiling point of the reaction mixture;
   (c) introducing a halogenating agent which is one member selected from the group consisting of chlorine, bromine, and sulfuryl halides to the reaction mixture obtained in step (b); and
   (d) obtaining a para-monohalogeno-mono($C_{1-4}$)alkylbenzene.

16. A process for obtaining with high selectivity a para-monhalogeno-mono($C_{1-4}$)alkylbenzene from a mono($C_{1-4}$)alkylbenzene, said process comprising:
   (a) combining (a1) an L-type zeolite of the formula

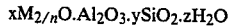

$xM_{2/n}O \cdot Al_2O_3 \cdot ySiO_2 \cdot zH_2O$ wherein M is at least one member selected from the group consisting of potassium ion, sodium ion and metal ions of groups IA, IIA, IIIV, IVA, and VA of the Periodic Table of the Elements, n is the valence of M, x is a number between 0.9 and 1.3, y is a number between 4.0 and 8.0, and z is a number between 0 to about 9, and (a2) a mono-($C_{1-4}$)alkylbenzene to obtain a reaction mixture;
   (b) adjusting the temperature of the said reaction mixture to a temperature between 0° C. and 90° C.;
   (c) introducing a halogenating agent to the reaction mixture obtained in step (b), where the halogenating agent is chlorine, bromine, a sulfuryl halide, or a mixture of these; and
   (d) obtaining a para-monohalogeno-mono($C_{1-4}$)alkylbenzene as the primary product.

17. The process of claim 16, comprising
   (a) combining toluene and a L-type zeolite to obtain a reaction mixture; wherein the L-type zeolite has an average micropore diameter of 8 Å and the following composition: $SiO_2=64.6\%$ by weight; $Al_2O_3=17.8\%$ by weight; $Na_2O=0.15\%$ by weight; $SiO_2/Al_2O_3$ (molar ratio)$=6.2$; and $K_2O=15.9\%$ by weight;
   (c) introducing chlorine to the reaction mixture; and
   (d) obtaining p-chlorotoluene as the primary product.

18. The process of claim 16, comprising:
   (a) combining toluene and a L-type zeolite to obtain a reaction mixture; wherein the L-type zeolite has an average micropore diameter of 8 Å and a composition as follows: $SiO_2=62.6\%$ by weight (dry basis); $Al_2O_3=18.0\%$ by weight; $Na_2O=0.097\%$ by weight; $SiO_2/Al_2O_3$ (molar ratio)$=5.9$; and $K_2O=28.6\%$ by weight (dry basis);
   (c) introducing chlorine to the reaction mixture; and
   (d) obtaining p-chlorotoluene as the primary product.

19. The process of claim 16, comprising:
   (a) combining toluene and a L-type zeolite to obtain a reaction mixture; wherein the L-type zeolite has an average micropore diameter of 8 Å and a composition as follows: $SiO_2=63.2\%$ by weight (dry basis); $Al_2O_3=17.6\%$ by weight; $Na_2O=0.1\%$ by weight; $SiO_2/Al_2O_3$ (molar ratio)$=6.1$; and $K_2O=17.6\%$ by weight (dry basis);
   (c) introducing chlorine to the reaction mixture; and
   (d) obtaining p-chlorotoluene as the primary product.

20. The process of claim 16, comprising:
   (a) combining toluene and a L-type zeolite to obtain a reaction mixture, wherein the L-type zeolite has an average micropore diameter of 8 Å and a composition as follows: $SiO_2=64.1\%$ by weight (dry basis); $Al_2O_3=18.4\%$ by weight; $Na_2O=0.202\%$ by weight; $SiO_2/Al_2O_3$ (molar ratio)$=5.9$; and $K_2O=17.6\%$ by weight (dry basis);
   (c) introducing chlorine to the reaction mixture; and
   (d) obtaining p-chlorotoluene as the primary product.

21. The process of claim 16, comprising:
   (a) combining ethylbenzene, isopropylbenzene, sec-butylbenzene, tert-butylbenzene, or a mixture thereof with a L-type zeolite to obtain a reaction mixture; wherein the L-type zeolite has an average micropore diameter of 8 Å and a composition as follows: $SiO_2=64.6\%$ by weight; $Al_2O_3=17.8\%$ by weight; $Na_2O=0.15\%$ by weight; $SiO_2/Al_2O_3$ (molor ratio)$=6.2$; and $K_2O=15.9$ by weight;
   (c) introducing chlorine to the reaction mixture; and
   (d) obtaining a para-chloro-mono-($C_2$-$C_3$)alkylbenzene as the primary product.

* * * * *

UNITED STATES PATENT AND TRADEMARK OFFICE
CERTIFICATE OF CORRECTION

PATENT NO. : 4,794,201
DATED : December 27, 1988
INVENTOR(S) : Yasushi HIGUCHI, et al It is certified that error appears in the above-identified patent and that said Letters Patent is hereby corrected as shown below:

On the title page
--Please insert Priority Information. It should read:

12-22-82  [JP]Japan......57-225259
    5-13-83   [JP]Japan......58-083677--

--[63] The filing date for Continuation Application
   Serial Number 06/758,250 is incorrect. It should
   read:

July 24, 1985   not

January 24, 1985.--

Signed and Sealed this

Sixth Day of June, 1989

Attest:

DONALD J. QUIGG

Attesting Officer

Commissioner of Patents and Trademarks